United States Patent
Satake et al.

(10) Patent No.: US 9,962,074 B2
(45) Date of Patent: May 8, 2018

(54) OPHTHALMIC IMAGING DEVICE AND OPHTHALMIC IMAGING PROGRAM

(71) Applicant: NIDEK CO., LTD., Gamagori, Aichi (JP)

(72) Inventors: Norimasa Satake, Aichi (JP); Ai Takaya, Shizuoka (JP)

(73) Assignee: NIDEK CO., LTD., Gamagori, Aichi (JP)

(*) Notice: Subject to any disclaimer, the term of this patent is extended or adjusted under 35 U.S.C. 154(b) by 75 days.

(21) Appl. No.: 15/255,332

(22) Filed: Sep. 2, 2016

(65) Prior Publication Data

US 2017/0065171 A1    Mar. 9, 2017

(30) Foreign Application Priority Data

Sep. 4, 2015    (JP) ................. 2015-175117

(51) Int. Cl.
*A61B 3/14*    (2006.01)
*A61B 3/00*    (2006.01)
*A61B 3/10*    (2006.01)

(52) U.S. Cl.
CPC ............ *A61B 3/102* (2013.01); *A61B 3/0025* (2013.01); *A61B 3/0041* (2013.01); *A61B 3/0091* (2013.01); *A61B 3/14* (2013.01)

(58) Field of Classification Search
CPC ......... A61B 3/102; A61B 3/14; A61B 3/0025; A61B 3/0041; A61B 3/0091
USPC .................................................. 351/206, 246
See application file for complete search history.

(56) References Cited

U.S. PATENT DOCUMENTS

2015/0168127 A1    6/2015    Takeno et al.

FOREIGN PATENT DOCUMENTS

JP          2015131107 A          7/2015

*Primary Examiner* — Jack Dinh
(74) *Attorney, Agent, or Firm* — Sughrue Mion, PLLC

(57) ABSTRACT

An ophthalmic imaging device that captures an image of a test eye, the device includes: an OCT optical system configured to acquire an OCT signal by scanning a tissue of the test eye with measurement light, the ophthalmic imaging device configured to execute: receiving a designation of a wide area which is wider than a unit area which is an acquisition unit for acquiring motion contrast data indicating a motion of the tissue; acquiring a plurality of OCT signals for the same position at different timing in each of a plurality of unit areas, the plurality of unit areas being positioned in the designated wide area and being not completely overlapped with each other; and acquiring the motion contrast data of each of the plurality of unit areas by processing the plurality of OCT signals acquired for the same position.

18 Claims, 7 Drawing Sheets

US 9,962,074 B2

OPHTHALMIC IMAGING DEVICE AND OPHTHALMIC IMAGING PROGRAM

CROSS REFERENCE TO RELATED APPLICATION

This application is based upon and claims the benefit of priority of Japanese Patent Application No. 2015-175117 filed on Sep. 4, 2015, the contents of which are incorporated herein by reference in its entirety.

BACKGROUND

This disclosure relates to an ophthalmic imaging device that captures images of a test eye, and to an ophthalmic imaging program.

The related art discloses an ophthalmic imaging device, which acquires an optical coherence tomography (OCT) signal by splitting light from a light source into measurement light and reference light, and processing an interference signal induced by the reference light and measurement light with which a test object is irradiated and then which is reflected by the test object. An optical coherence tomography device disclosed in JP-A-2015-131107 generates motion contrast data by processing a plurality of OCT signals which are taken for the same position on a test object at different timing.

SUMMARY

The operation of an ophthalmic imaging device when acquiring motion contrast data is different from the operation of merely acquiring tomographic image data of a test object. In the related art, it is difficult to easily acquire a wide range of motion contrast data via an ophthalmic imaging device.

A typical object of this disclosure is to provide an ophthalmic imaging device that is capable of easily acquiring a wide range of motion contrast data, and an ophthalmic imaging program.

An aspect of the present disclosure provides the following arrangements:

An ophthalmic imaging device that captures an image of a test eye, the device comprising:
  an OCT optical system configured to acquire an OCT signal by scanning a tissue of the test eye with measurement light;
  a processor; and
  a memory storing computer readable instructions, when executed by the processor, causing the ophthalmic imaging device to execute:
    a wide area receiving instruction of receiving a designation of a wide area which is wider than a unit area which is an acquisition unit for acquiring motion contrast data indicating a motion of the tissue;
    a unit OCT signal acquisition instruction of acquiring a plurality of OCT signals for the same position at different timing in each of a plurality of unit areas, the plurality of unit areas being positioned in the designated wide area and being not completely overlapped with each other; and
    a unit data acquisition instruction of acquiring the motion contrast data of each of the plurality of unit areas by processing the plurality of OCT signals acquired for the same position.

A non-transitory computer readable recording medium storing an ophthalmic imaging program that is executed by a control device which controls an operation of an ophthalmic imaging device configured to capture an image of a test eye, wherein the ophthalmic imaging device includes an OCT optical system configured to acquire an OCT signal by scanning a tissue of the test eye with measurement light, the ophthalmic imaging program, when executed by the control device of the ophthalmic imaging device, causing the ophthalmic imaging device to execute:
  receiving a designation of a wide area which is wider than a unit area which is an acquisition unit for acquiring motion contrast data indicating a motion of the tissue:
  acquiring a plurality of OCT signals for the same position at different timing in each of a plurality of unit areas, the plurality of unit areas being positioned in the designated wide area and being not completely overlapped with each other; and
  acquiring the motion contrast data of each of the plurality of unit areas by processing the plurality of OCT signals acquired for the same position,
  wherein motion contrast data of a range of area wider than each unit area is acquired by positioning the plural pieces motion contrast data acquired from each of the plurality of unit areas.

DESCRIPTION OF ILLUSTRATIVE EMBODIMENTS

Hereinafter, one typical embodiment of this disclosure will be described. Hereinafter, a case, in which motion contrast data of fundus tissues of a test eye is acquired, is illustrated. Technology exemplified in this disclosure can be applied to a case in which motion contrast data of tissues other than a fundus is acquired. Motion contrast data represents data illustrating a motion in a tissue (for example, the flow of blood flowing through a blood vessel of a tissue, or the flow of a lymph fluid in a tissue). In the embodiment, motion contrast data is acquired by acquiring a plurality of OCT signals for the same position on a tissue at different timings, and processing the plurality of acquired OCT signals.

<Schematic Entire Configuration of Device>

Figure 1:
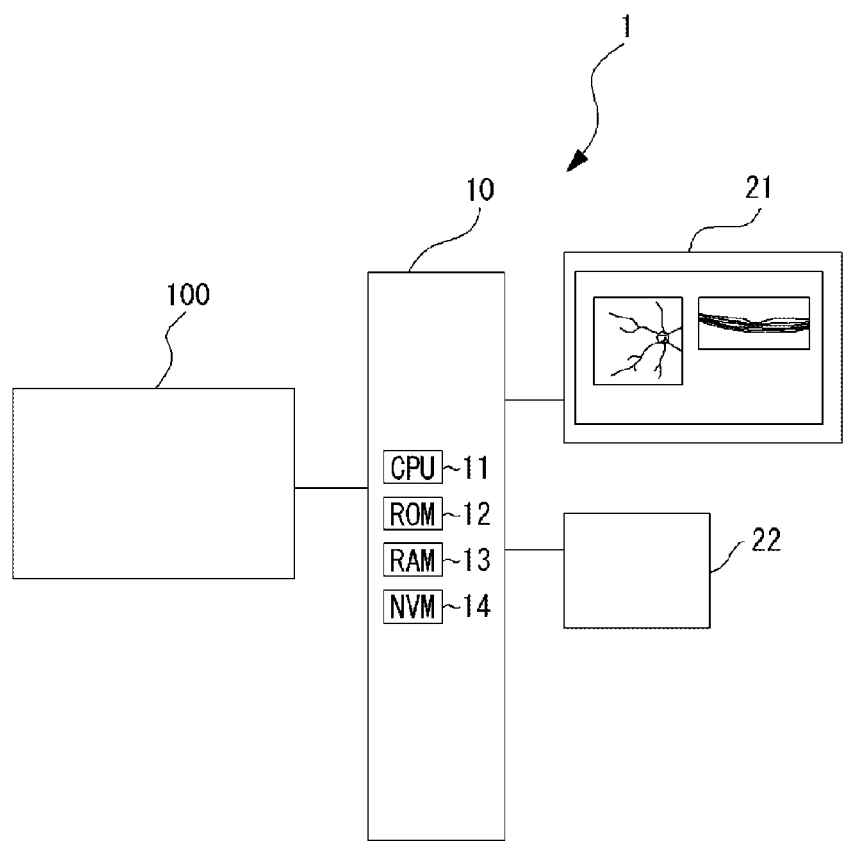
FIG. 1 is a schematic block diagram illustrating the configuration of an ophthalmic imaging device 1 of an embodiment.

The schematic configuration of the ophthalmic imaging device 1 of the embodiment will be described with reference to FIG. 1. The ophthalmic imaging device (optical coherence tomography device) 1 of the embodiment acquires signals (for example, OCT signals) via an OCT optical system (interference optical system) 100, and processes the acquired signals. The ophthalmic imaging device 1 of the embodiment is capable of displaying an image, which is captured by the OCT optical system 100, on a display (for example, monitor) 21. The ophthalmic imaging device 1 of the embodiment includes the OCT optical system 100; a control unit 10; the display 21; and an operation unit 22.

The control unit 10 controls the operation of the ophthalmic imaging device 1. The control unit 10 of the embodiment includes a processor (CPU) 11; a ROM 12, a RAM 13, and a non-volatile memory (NVM) 14. The CPU 11 controls each part of the ophthalmic imaging device 1. The ROM 12 stores various programs, initial values, and the like. The RAM 13 temporarily stores various information. The non-volatile memory 14 is a non-transient storage medium that is capable of holding stored contents even if the supply of electric power is shut off. For example, a hard disk drive, a flash ROM, and a detachable USB memory may be used as the non-volatile memory 14. In the embodiment, the non-volatile memory 14 stores an ophthalmic imaging program for executing a panorama mode process (to be described later) (refer to FIG. 4) and the like.

The embodiment exemplifies the integral ophthalmic imaging device 1 in which the OCT optical system 100, the control unit 10, and the like are built into one housing. Needless to say, the ophthalmic imaging device 1 may include multiple devices including different housings. For example, the ophthalmic imaging device 1 may include an optical device with the built-in OCT optical system 100, and a personal computer (hereinafter, referred to as a "PC") that is connected to the optical device via wires or wirelessly. In this case, a control unit of the optical device and a control unit of the PC may serve as the control unit 10 of the ophthalmic imaging device 1. That is, the control unit 10 may include multiple processors. Similarly, the control unit 10 may include multiple non-volatile memories 14. The control unit of the PC alone may serve as the control unit 10 of the ophthalmic imaging device 1. A commercially available PC may be used as a portion of the ophthalmic imaging device 1. In this case, at least a portion of the ophthalmic imaging program can be installed in the commercially available PC.

The display 21 may be a display mounted in a device main body, or may be a display separate from the device main body. For example, if the ophthalmic imaging device 1 is a device in which an optical device with the built-in OCT optical system 100 and a PC are assembled together, a display of the PC may be used as the display 21. The display 21 may be a touch panel. In this case, the display 21 may serve as the operation unit 22. The operation unit 22 outputs a signal to the control unit 10 according to an input operation instruction. At least one of a mouse, a joystick, a keyboard, a touch panel, and the like may be used as the operation unit 22.

<OCT Optical System>

Figure 2:
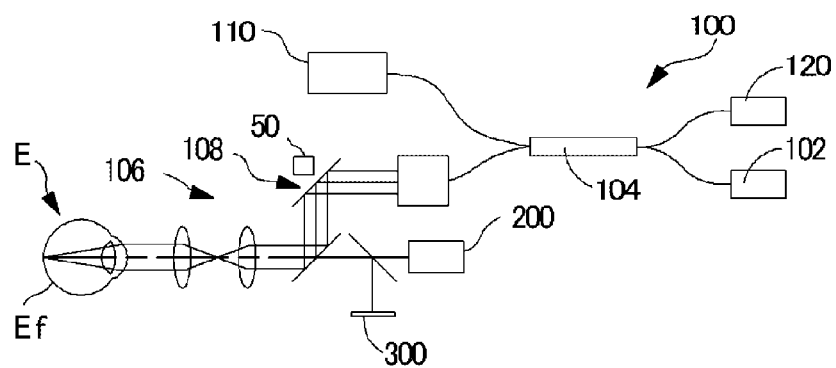
FIG. 2 is a block diagram illustrating the configuration of an OCT optical system 100 of the embodiment.

The OCT optical system 100 will be described with reference to FIG. 2. The OCT optical system 100 has the configuration of a so-called ophthalmic optical coherence tomography (OCT) device, and is capable of capturing a tomographic image of a test eye E. The OCT optical system 100 splits light, which is emitted from a measurement light source 102, into measurement light (specimen light) and reference light via a coupler (light splitter) 104. The OCT optical system 100 guides the measurement light to a tissue (fundus Ef in the embodiment) of the eye E via a measurement optical system 106, and guides the reference light to a reference optical system 110. A light receiving element (detector) 120 of the OCT optical system 100 receives interference light which is a combination of the reference light and measurement light that is reflected by the tissue.

The light receiving element 120 detects an interference signal induced by the measurement light and the reference light. If Fourier domain OCT is used, the spectral intensity (spectral interference signal) of the interference light is detected by the light receiving element 120, and complex OCT signals are acquired by transforming spectral intensity data via Fourier transform.

For example, if Fourier domain OCT is used, a predetermined range of depth profile (A scan signal) is acquired by calculating an absolute value of an amplitude of the complex OCT signals acquired by transforming the spectral intensity data via Fourier transform. OCT image data (tomographic image data) is acquired by aligning depth profiles for the scan positions of measurement light scanned by an optical scanner (example of a scanning unit that scans a tissue with measurement light) 108. The ophthalmic imaging device 1 may acquire three-dimensional OCT image data (three-dimensional tomographic image data) by scanning the tissue with measurement light in a two-dimensional direction. OCT enface image data for a case where the tissue is viewed from a direction (enface direction) along an optical axis of the measurement light may be acquired from the three-dimensional OCT image data. The OCT enface image data may be integrated image data obtained by integrating luminance values in a depth direction (Z direction) for positions in an XY direction, an integrated value of spectral data for positions in the XY direction, luminance data in a certain depth direction for each position in the XY direction, luminance data for each position on a layer (for example, outer retinal layer) of a retina in the XY direction, or the like.

Motion contrast data is acquired from two or more OCT signals which are acquired from the same portion of the tissue at different timings (different times). That is, motion contrast data is acquired by analyzing a plurality of complex OCT signals. For example, two-dimensional motion contrast data is acquired by aligning motion contrast data for measurement points of measurement light scanned along one scanning line. Three-dimensional motion contrast data is acquired by scanning measurement light in the XY direction (that is, two-dimensional direction along the optical axis of the measurement light). Enface motion contrast data for a case where the tissue is en face viewed is acquired from the three-dimensional motion contrast data. The enface motion contrast data may be Doppler enface image data, signal image data, speckle variance enface image data, or the like. A method of acquiring motion contrast data will be described in detail later.

Spectral-domain-OCT (SD-OCT), swept-source-OCT (SS-OCT), or the like can be adopted as an example of Fourier domain OCT. Time-domain-OCT (TD-OCT) or the like can be also adopted. If SD-OCT is adopted, a low coherent light source (broadband light source) is used as the measurement light source 102, and a spectrometer is provided in the vicinity of the light receiving element 120 on an optical path of the interference light, and spectralizes the interference light into frequency components (wavelength components). If SS-OCT is adopted, a wavelength scanning light source (variable wavelength light source), which changes emitted wavelengths at a high speed in time, is used as the measurement light source 102. In this case, the measurement light source 102 may include a light source; a fiber ring resonator; and a wavelength selection filter. Examples of the wavelength selection filter include a filter in which a diffraction grating and a polygon mirror are assembled together, and a filter using a Fabry-Perot etalon.

Light emitted from the measurement light source 102 is split into measurement light fluxes and reference light fluxes by the coupler 104. After having passed through an optical fiber, the measurement light is emitted to the air. The measurement light emitted to the air concentrates on the tissue (the fundus Ef in the embodiment) via the optical scanner 108 and the like of the measurement optical system 106. The measurement light reflected by the tissue returns to the optical fiber through the same optical path.

The optical scanner 108 scans the tissue with the measurement light in the two-dimensional direction (XY direction). The optical scanner 108 of the embodiment is arranged at a position substantially conjugate to that of a pupil of the test eye E. For example, the optical scanner 108 of the embodiment includes two galvanometer mirrors. The reflection angles of the galvanometer mirrors are arbitrarily adjusted by a drive mechanism 50. As a result, the reflection direction of the measurement light emitted from the measurement light source 102 is changed, and an arbitrary position on the tissue is irradiated with the measurement light. That is, the irradiation position of the measurement light on the tissue is changed by the optical scanner 108. Needless to say, the configuration of the optical scanner 108 can be changed. For example, a polygon mirror, a resonant scanner, an acousto-optic modulator (AOM), or the like may be adopted in the optical scanner 108.

The reference optical system 110 generates reference light that is combined with the measurement light reflected by the tissue. The reference optical system 110 may be a Michelson type system, or a Mach-Zehnder type system. The reference optical system 110 of the embodiment reflects light, which is incident from the coupler 104, via a reflecting optical system (for example, reference mirror) such that the light is returned to the coupler 104 again and is guided to the light receiving element 120. The configuration of the reference optical system 110 can be also changed. For example, the reference optical system 110 may guide light, which is incident from the coupler 104, to the light receiving element 120 by transmitting the light rather than reflecting the light. The reference optical system 110 is capable of changing a difference in optical path length between the measurement light and the reference light by moving an optical member on the optical path. In the embodiment, a difference in optical path length is changed by moving a reference mirror in an optical axis direction. A configuration element for changing a difference in optical path length may be provided on the optical path of the measurement optical system 106.

<Enface Observation Optical System>

An enface observation optical system 200 acquires enface image data of a test eye. The enface image data may be complete two-dimensional image data, or may be signal data for each measurement point which is used to calculate the luminance of each pixel of a two-dimensional image. The enface observation optical system 200 is capable of acquiring enface image data of a tissue (the fundus Ef in the embodiment) of the test eye. For example, the enface observation optical system 200 of the embodiment includes an optical scanner that scans the tissue with measurement light (for example, infrared light), which is emitted from a light source, in the two-dimensional direction (XY direction), and a light receiving element that receives reflected light via a confocal opening arranged at a position substantially conjugate to the position of the tissue. That is, the enface observation optical system 200 of the embodiment has the configuration of a so-called ophthalmic scanning laser ophthalmoscope (SLO).

The configuration of the enface observation optical system 200 can be changed. For example, the enface observation optical system 200 may have the configuration of a so-called fundus camera. The enface observation optical system 200 may include an infrared imaging optical system that acquires (captures) an enface image of a tissue of the test eye E by collectively irradiating a two-dimensional imaging range of the tissue with infrared light rather than scanning the two-dimensional imaging range with measurement light. The enface observation optical system 200 of the embodiment is assembled into the OCT optical system 100. Alternatively, the OCT optical system 100 and the enface observation optical system 200 may be separately provided.

<Fixation Target Presentation Optical System>

A fixation target presentation optical system 300 guides a line-of-sight direction of the test eye E by presenting a fixation target to the test eye E. For example, the fixation target presentation optical system 300 of the embodiment includes a visible light source that emits visible light, and is capable of changing the presentation position of the fixation target with respect to the test eye E in the XY direction. As a result, the line-of-sight direction of the test eye E is changed, and an imaged portion is changed. For example, the fixation target presentation optical system 300 may change the line-of-sight direction of the test eye E by switching the light positions of LEDs which are arranged in a matrix pattern. The fixation target presentation optical system 300 may change the line-of-sight direction by scanning light from the visible light source via the optical scanner, and controlling the lighting of the visible light source. The fixation target presentation optical system 300 may be an internal fixation lamp type system that presents a fixation target from the inside of a device, or may be an external fixation lamp type system that presents a fixation target from the outside of a device.

<Method of Acquiring Motion Contrast Data>

An example of the operation of acquiring motion contrast data from an OCT signal and a computational process will be described with reference to FIG. 3. In order to acquire motion contrast data, the control unit 10 (CPU 11) of the embodiment acquires at least two frames of OCT signals (interference signals) measured at different timing by scanning the same position on a tissue with measurement light a plurality of times. The control unit 10 acquires motion contrast data by computing the acquired OCT signals.

Examples of a method of acquiring motion contrast data via processing of OCT signals include a method of calculating a phase difference between complex OCT signals, a method of calculating a vector difference between complex OCT signals, and a method of multiplying together a phase difference and a vector difference between complex OCT signals. Hereinafter, for example, the method of performing a process via a Doppler phase difference method and a process via a vector difference method, and multiplying together a phase difference and a vector difference will be described.

Figure 3:
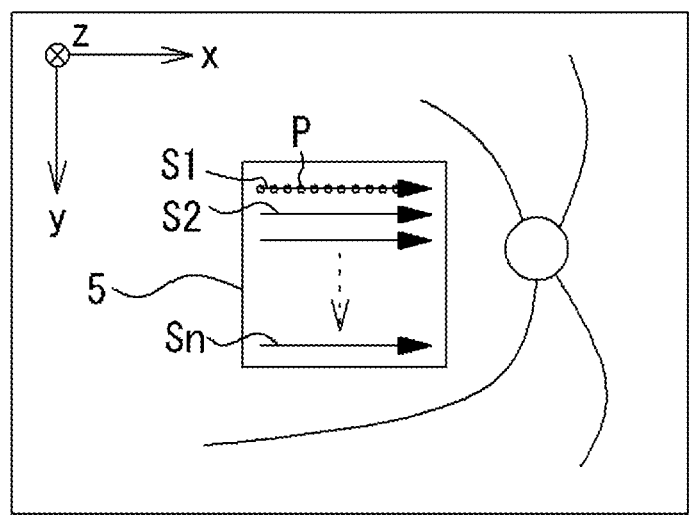
FIG. 3 is a view illustrating the operation of acquiring OCT signals.

As illustrated in FIG. 3, in the embodiment, a unit area 5 which is an acquisition unit for acquiring motion contrast data is set. The unit area 5 exemplified in FIG. 3 is a two-dimensional area having a square shape when viewed in the Z direction (enface direction). The shape of the unit area 5 can be changed. For example, the unit area 5 may have a rectangular shape, or may have a circular shape, an elliptical shape, or the like. In a case where three-dimensional motion contrast data or enface motion contrast data is acquired from the unit area 5, the unit area 5 becomes a two-dimensional area.

As illustrated in FIG. 3, the control unit 10 scans measurement light a plurality of times along each of multiple scanning lines S (S1 to Sn) in the unit area 5. As a result, OCT signals, the number of which is the same as the number of scans, are acquired for the same position where each scanning line S is arranged. In an example illustrated in FIG. 3, each scanning line S extends straight in an X direction, and the plurality of scanning lines S having the same length are aligned in a Y direction such that the entirety of the unit area 5 is scanned with measurement light. The shape of the scanning line S and the disposition of scanning lines S can be also changed. For example, the straight scanning line S may extend in the Y direction, or may extend in an oblique direction. The scanning lines S may have different lengths. The plurality of scanning lines S may intersect each other. Non-straight (for example, annular, curved, or bent) scanning lines may be adopted.

An OCT signal is acquired for each of a plurality of measurement points P on each scanning line S. For example, in a case where the scanning speed of measurement light on the scanning line S is constant, and the light receiving element 120 (refer to FIG. 2) of the OCT optical system 100 detects a received light signal at constant intervals, as illustrated in FIG. 3, the interval between the measurement points P on the scanning line S becomes constant. The measurement points P are schematically illustrated in FIG. 3, the size of the measurement point P, the interval between the measurement points P, the number of measurement points P, and the like illustrated in FIG. 3 are different from actual ones.

If the number of measurement points P on the scanning lines S is increased, the number of pixels in a motion contrast image (image generated from motion contrast data) acquired from the unit area 5 is increased. In order to acquire good motion contrast data, the same position is desirably scanned with measurement light at suitable time intervals (for example, every 2.5 ms to 5 ms) a plurality of times. There is a limit to the speed (that is, the number of times where received light signals can be detected per unit time) of the light receiving element 120 at which the light receiving element 120 is capable of detecting received light signals. The performance of the optical scanner 108, the capacity of the memory, or the like may limit an increase in the number of measurement points P on the scanning line S. In the embodiment, an upper limit value for the number of measurement points P on the scanning line S is determined by effects of such various factors. For example, in the embodiment, an upper limit value for the number of measurement points P on the scanning line S is 256. If the number of measurement points P on the scanning line S is set to 256, and 256 scanning lines S are set to be aligned in a direction intersecting a scanning direction in the unit area 5 having a square shape, motion contrast data is acquired for each of "256 in a longitudinal direction×256 in a lateral direction" measurement points. The upper limit value may be suitably set according to the speed at which the light receiving element 120 is capable of detecting received light signals.

The number of measurement points P on the scanning line S can be set to be less than the upper limit value. For example, in the embodiment, the number of measurement points P on the scanning line S may be set to 128. In this case, the control unit 10 is also capable of acquiring OCT signals from each of two scanning lines S at suitable time intervals by scanning each of the two scanning lines S with measurement light once, and then scanning the two scanning lines S with measurement light again.

The control unit 10 transforms the OCT signals, which are acquired by the OCT optical system 100, via Fourier transform. As a result, complex OCT signals are obtained. The complex OCT signal contains a rear number component and an imaginary number component. Subsequently, the control unit 10 calculates a phase difference from a plurality of complex OCT signals which are acquired for the same position at different timings. The control unit 10 removes random phase differences which are present in an area having a low S/N ratio (signal to noise ratio). As a result, reflected signals induced by a high reflection portion are removed, and thus, it is easy to distinguish between signals from the high reflection portion and signals from a blood vessel and the like. In the embodiment, one frame from which a phase difference is calculated is acquired. In a case where multiple frames from which phase differences are calculated are present, the control unit 10 may reduce noise of multiple frames of signals via an arithmetic averaging process.

Subsequently, the control unit 10 calculates a vector difference between the complex OCT signals. A complex OCT signal can be represented as a vector on a complex plane. Contrast image data of the test eye E is generated by calculating a vector difference between the plurality of signals which are acquired for the same position at different timing. The vector difference may be imaged based on phase information other than the size of the difference. In the embodiment, one frame from which a vector difference is calculated is acquired. In a case where multiple frames from which vector differences are calculated are present, the control unit 10 may reduce noise of multiple frames of signals via an arithmetic averaging process.

In the embodiment, the control unit 10 uses the result of the calculation of the phase difference as a filter for the result of the calculation of the vector difference. The "use of a calculation result as a filter" implies that weighting is applied to a certain numerical value. For example, the control unit 10 performs weighting by multiplying the result of the calculation of the vector difference by the result of the calculation of the phase difference. As a result, the vector difference of a portion having a small phase difference is decreased, and the vector difference of a portion having a large phase difference is increased. Adverse effects of each calculation method are reduced by multiplying together the result of the calculation of the vector difference and the result of the calculation of the phase difference, and better motion contrast data is acquired.

The control unit 10 is capable of acquiring three-dimensional motion contrast data by computing the plurality of OCT signals acquired from each of the plurality of scanning lines S. The control unit 10 is capable of acquiring enface motion contrast data from the three-dimension motion contrast data. For example, the enface motion contrast data may be used as a pseudo blood vessel contrast image. The motion contrast data may be complete image data, or may be values used to calculate the luminance of each pixel of an image.

In the embodiment, motion contrast data is acquired for each unit area 5. The control unit 10 of the embodiment is capable of acquiring motion contrast data of a range of area wider than the unit area 5 by acquiring motion contrast data from each of the plurality of unit areas 5 which are not completely overlapped with each other. This process will be described in detail later.

A computational processing method for acquiring motion contrast data is not limited to the aforementioned method. For example, motion contrast data may be acquired using a result of the calculation of a vector difference, or may be acquired using a result of the calculation of a phase difference. Motion contrast data may be acquired using a result of a difference in amplitude, amplitude-decorrelation, speckle variance, phase variance, or the like.

<Process of Acquiring Wide Range of Motion Contrast Data>

A process of acquiring a wide range of motion contrast data will be described with reference to FIGS. 4 to 11. A wide range of motion contrast data is motion contrast data that is acquired from at least a portion of a wide area 6 wider than the unit area 5. A wide range of motion contrast data can be also referred to as panorama motion contrast data. If an instruction to start a panorama mode is input into the ophthalmic imaging device 1, the CPU 11 of the ophthalmic imaging device 1 of the embodiment executes a panorama mode process illustrated in FIG. 4 according to an ophthalmic imaging program. For example, an instruction to start a panorama mode may be input by operating a panorama mode button displayed on the display 21.

Figure 4:
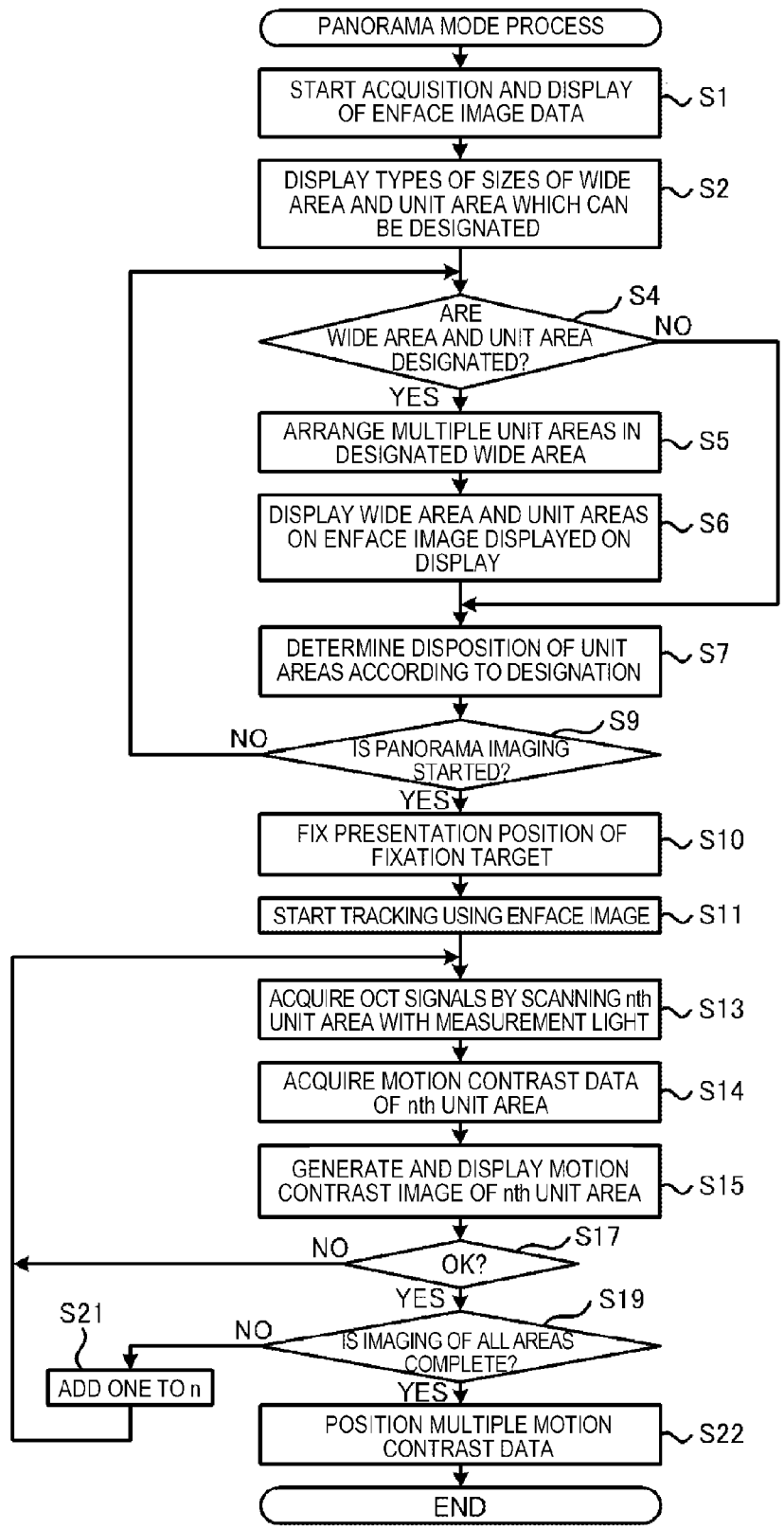
FIG. 4 is a flowchart illustrating a panorama mode process executed by the ophthalmic imaging device 1.

As illustrated in FIG. 4, if the panorama mode process is started, the CPU 11 starts to acquire enface image data of a tissue (the fundus Ef in the embodiment), and starts to display an enface image on the display 21 (S1). As described above, enface image data is acquired by the enface observation optical system 200. In the embodiment, the CPU 11 displays an enface image on an enface image display section (refer to FIGS. 5 to 9) of the display 21 based on the acquired enface image data. In the embodiment, enface image data of a range of area wider than each unit area 5 is acquired. In a state where a still enface image is displayed, the CPU 11 of the embodiment executes a process (S4 to S9) for setting a method of acquiring a wide range of motion contrast data. Accordingly, in this case, a user can easily and suitably perform settings compared to a case where various setting are performed in a state where a moving enface image is displayed. The CPU 11 may execute the setting process in a state where a moving enface image is displayed.

Subsequently, the CPU 11 displays the sizes of multiple types of wide areas 6, which are selection candidates, on the display 21 (S2). The CPU 11 displays the sizes of multiple types of unit areas 5, which are selection candidates, on the display 21 (S2). In the embodiment, candidates for the sizes of the wide areas and the unit areas are determined in advance. In examples illustrated in FIGS. 5 to 9, a wide area designation section 66 displays three types of sizes, that is, "6 mm×6 mm", "9 mm×9 mm", and "12 mm×9 mm" as candidates for the size of the wide area 6. A unit area designation section 55 displays two types of sizes, that is, "3 mm×3 mm" and "4.5 mm×4.5 mm" as candidates for the size of the unit area 5.

Figure 5:
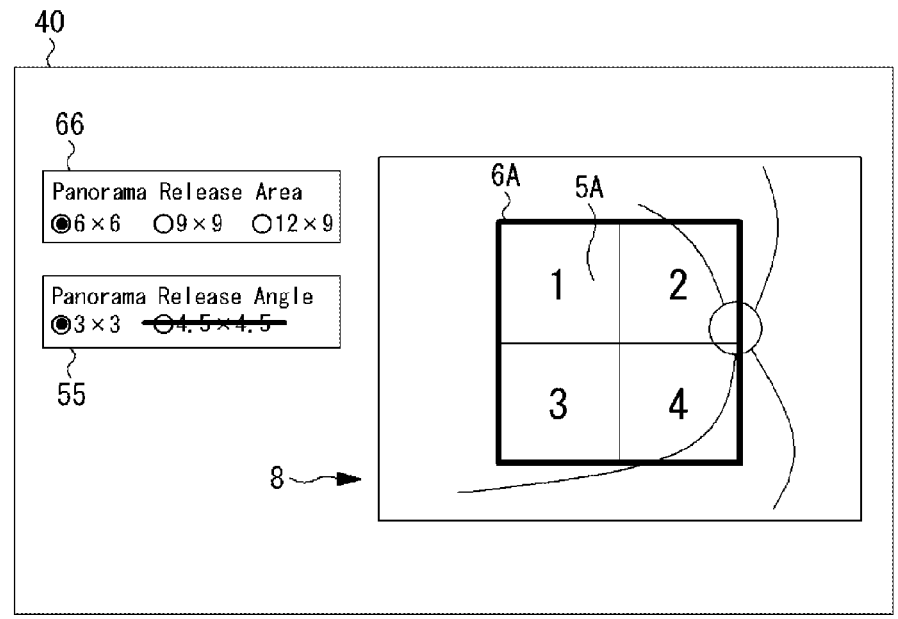
FIG. 5 is a view illustrating an example of a set screen 40 in a case where a wide area 6A of 6 mm×6 mm and a unit area 5A of 3 mm×3 mm are designated.
Figure 6:
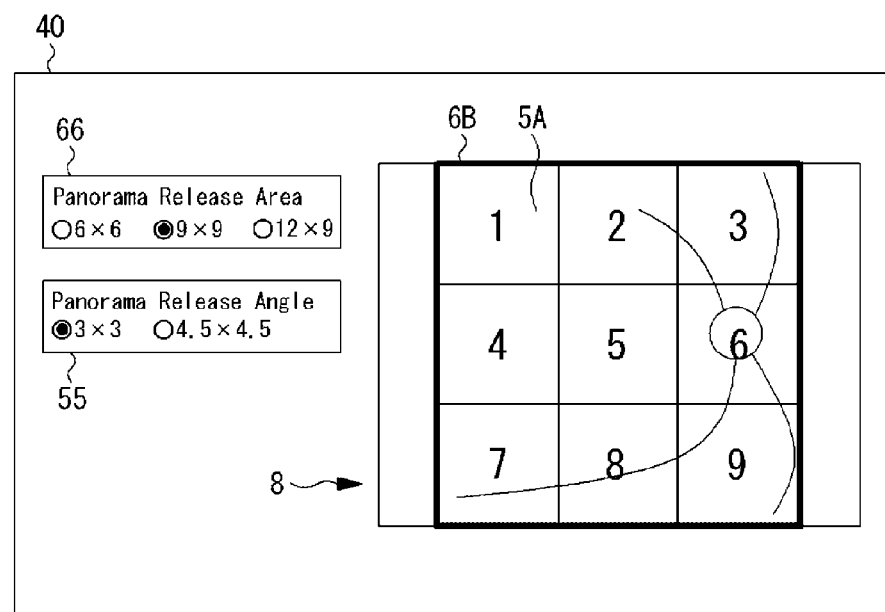
FIG. 6 is a view illustrating an example of the set screen 40 in a case where a wide area 6B of 9 mm×9 mm and the unit area 5A of 3 mm×3 mm are designated.
Figure 7:
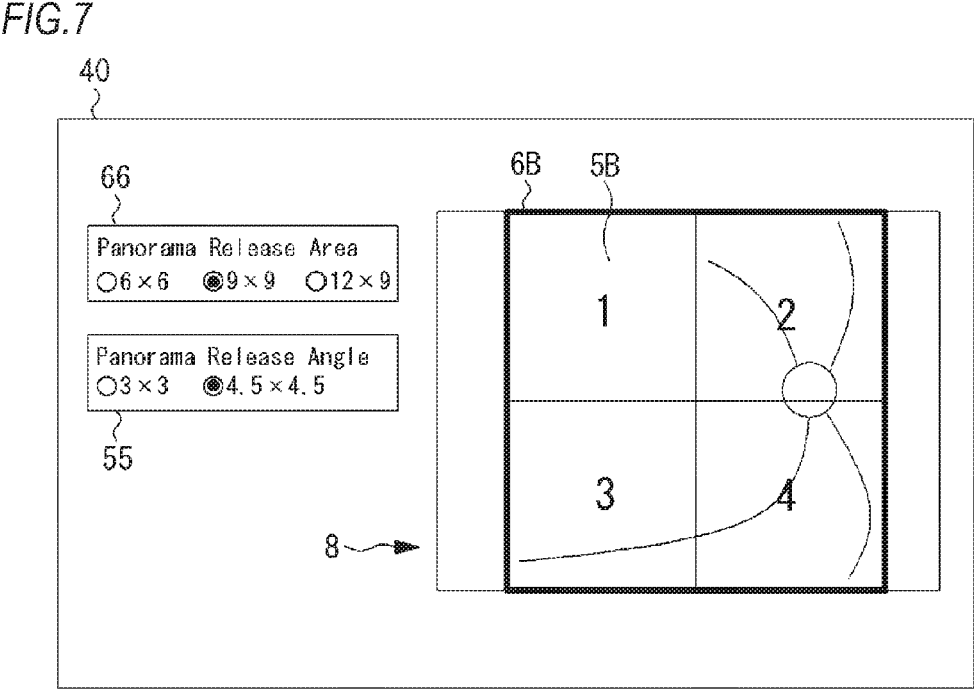
FIG. 7 is a view illustrating an example of the set screen 40 in a case where the wide area 6B of 9 mm×9 mm and a unit area 5B of 4.5 mm×4.5 mm are designated.
Figure 8:
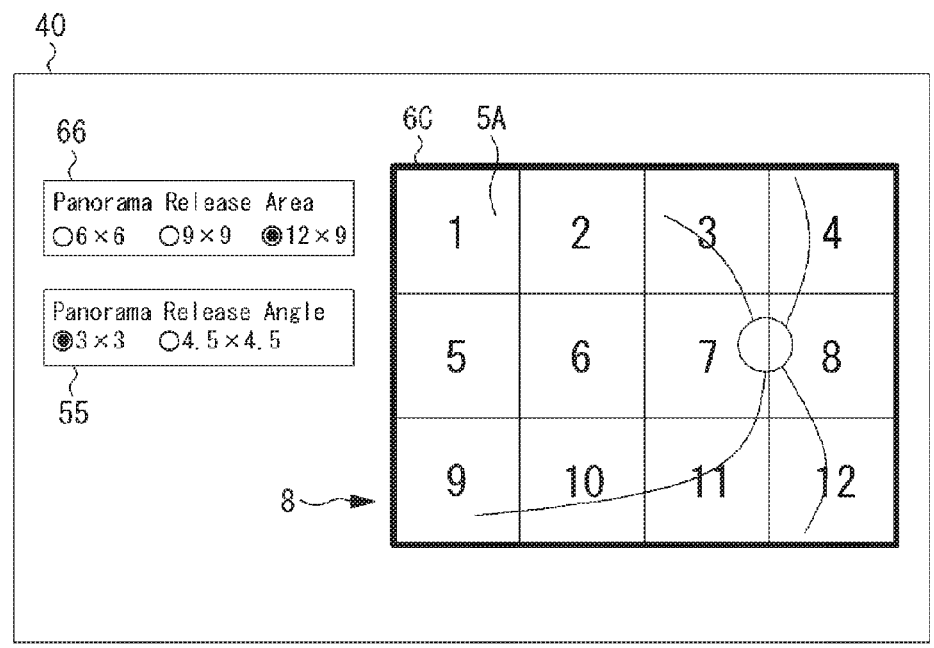
FIG. 8 is a view illustrating an example of the set screen 40 in a case where a wide area 6C of 12 mm×9 mm and the unit area 5A of 3 mm×3 mm are designated.
Figure 9:
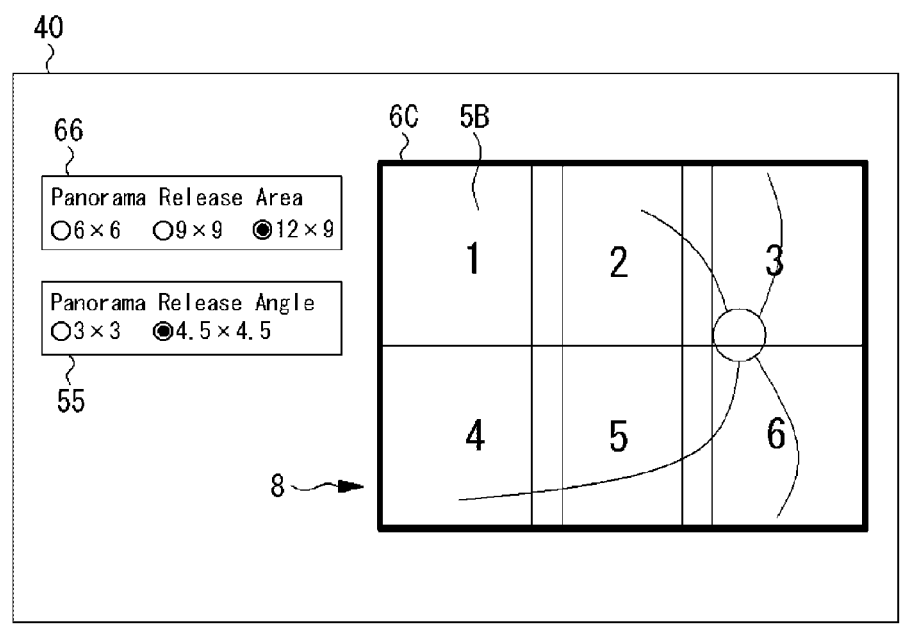
FIG. 9 is a view illustrating an example of the set screen 40 in a case where the wide area 6C of 12 mm×9 mm and the unit area 5B of 4.5 mm×4.5 mm are designated.
Figure 10:
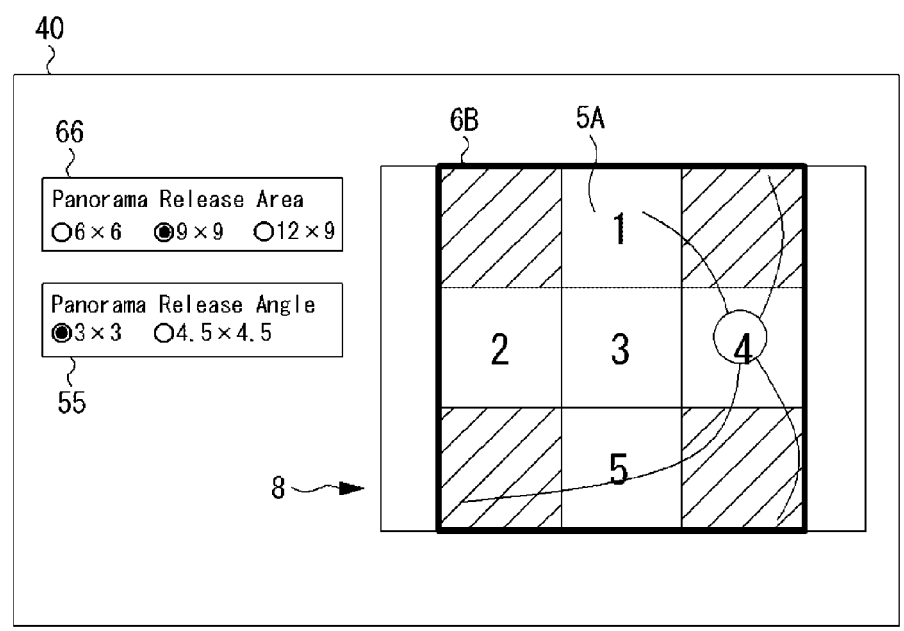
FIG. 10 is a view illustrating an example in which a user designates the disposition of unit areas 5.

In the embodiment, the types of the size of the unit area 5 which can be designated by a user are determined in advance according to the types of the size of the wide area 6. As illustrated in FIG. 5, if a wide area 6A of "6 mm×6 mm" is designated, only a unit area 5A of "3 mm×3 mm" can be designated. In contrast, as illustrated in FIGS. 6 and 7, if a wide area 6B of "9 mm×9 mm" is designated, both the area 5A of "3 mm×3 mm" and a unit area 5B of "4.5 mm×4.5 mm" can be designated. As illustrated in FIGS. 8 and 9, if a wide area 6C of "12 mm×9 mm" is designated, both the unit area 5A of "3 mm×3 mm" and the unit area 5B of "4.5 mm×4.5 mm" can be designated. Accordingly, in the ophthalmic imaging device 1 of the embodiment, a user can easily designate the size of the unit area 5 suitable for the size of each wide area 6.

Subsequently, the CPU 11 determines whether a user has designated the wide area 6 and the unit area 5 (S4). If the wide area 6 and the unit area 5 are not designated (S4: NO), the process proceeds to S7. If at least one of the wide area 6 and the unit area 5 is designated (S4: YES), the CPU 11 arranges a plurality of unit areas 5 in the designated wide area 6 (S5). The CPU 11 displays the wide area 6 and the unit areas 5 on an enface image displayed on the display 21 (S6). A method of displaying the wide area 6 and the unit areas 5 on the enface image can be suitably selected. For example, as in the embodiment, a frame indicating an area may be displayed on the enface image while being superimposed thereon. The color of a portion of the enface image corresponding to the inside of the area may be different from a color outside of the area.

An example of a method of arranging the unit areas 5 in the wide area 6 will be described with reference to FIGS. 5 to 9. The CPU 11 of the embodiment is capable of automatically arrange a plurality of unit areas 5 in the designated wide area 6 at positions where the plurality of unit areas 5 are not completely overlapped with each other (S5).

FIG. 5 illustrates a case in which the wide area 6A of "6 mm×6 mm" and the unit areas 5A of "3 mm×3 mm" are designated. In this case, the CPU 11 of the embodiment arranges four unit areas 5A in the wide area 6A in a matrix pattern such that end portions of adjacent unit areas 5A are aligned with each other. In the embodiment, also, in the examples illustrated in FIGS. 6 to 8, similarly, a plurality of unit areas 5 are arranged in the wide area 6 such that adjacent unit areas 5 adjoin each other. In the examples illustrated in FIGS. 5 to 8, candidates (that is, the types of a selectable size) for the sizes of the wide area 6 and the unit area 5 are determined such that the length of a side of the wide area 6 is divided by the length of a side of the unit area 5. Accordingly, if a plurality of unit areas 5 are arranged such that adjacent unit areas 5 adjoin each other, the plurality of unit areas 5 are arranged in the entire range of the wide area 6 in a state where there are no gaps therebetween. As a result, motion contrast data for the inside of the wide area 6 is more efficiently acquired.

FIG. 9 illustrates a case in which a wide area 6C of "12 mm×9 mm" and the unit areas 5B of "4.5 mm×4.5 mm" are designated. In this case, the CPU 11 of the embodiment arranges six unit areas 5B in a matrix pattern such that the unit areas 5B adjacent to each other in the lateral direction are partially overlapped with each other. The CPU 11 of the embodiment is capable of generating wide motion contrast images (two-dimensional image and three-dimensional image) using plural pieces of motion contrast data acquired from each unit area 5. In this case, if adjacent unit areas 5 are partially overlapped with each other, the CPU 11 is capable of reducing a difference in gradation between the unit areas 5 based on the gradation of the image in an overlapped portion. For example, the CPU 11 may adjust the gradation value of at least one motion contrast image such that a difference between the average gradation of an overlapped portion acquired from one unit area 5 and the average gradation of a overlapped portion acquired from the other unit area 5 is reduced.

The CPU 11 is capable of moving the positions of the wide area 6 and the plurality of unit areas 5 on the enface image according to an instruction input via the operation unit 22. In the embodiment, a user can move the wide area 6 and the plurality of unit areas 5, which are arranged in the wide area 6, on the enface image by dragging the wide area 6 via a mouse. In the embodiment, the plurality of unit areas 5 are arranged in the entire range of the wide area 6 in a state where there are no gaps therebetween. The wide area 6 may include a portion in which the unit area 5 is not arranged.

Returning to description of FIG. 4, the CPU 11 sets the positions of the plurality of unit areas 5, which are arranged in the wide area 6, according to an instruction from the user (S7). The user can input an instruction designating the positions of the unit areas 5 to the ophthalmic imaging device 1 by operating the operation unit 22. For example, the user can input an instruction, which invalidates the plurality of unit areas 5 arranged in the wide area 6 in S5, via the operation unit 22. In an example illustrated in FIG. 10, an instruction, which invalidates four unit areas 5 which are positioned at corners among nine unit areas 5 arranged in a matrix pattern, is input. In this case, the CPU 11 sets the positions of the plurality of unit areas 5 such that five validated unit areas 5 are aligned in a cross pattern. A method of setting the positions of the unit areas 5 according to an instruction from a user can be also changed. For example, the CPU 11 may move the position of each unit area 5 in the wide area 6 according to a drag operation via a mouse.

Subsequently, the CPU 11 determines whether an instruction to start the acquisition of motion contrast data (that is, an instruction to start panorama imaging) has been input (S9). If the instruction is not input (S9: NO), the process returns to S4, and the process of S4 to S9 is repeated. If the start instruction is input (S9: YES), the CPU 11 executes a process (S10 to S21) of acquiring a wide range of motion contrast data.

First, the CPU 11 fixes the presentation position of a fixation target with respect to the test eye E (S10). Subsequently, the CPU 11 starts the tracking of the unit areas 5 using the enface image data (S11). The CPU 11 of the embodiment repeatedly acquires enface image data from a range of area (for further details, a range of area containing all the plurality of unit areas 5 arranged in S5 and S7) wider than each unit area 5. The CPU 11 causes the positions (that is, positions to be scanned with measurement light) of the unit areas 5 on the tissue to track the positions set in S5 and S7 by using the enface image data. For further details, the CPU 11 compares enface image data, which is acquired in real time, to enface image data acquired before the acquisition of motion contrast data is started. The CPU 11 detects a change in relative position between the OCT optical system 100 and the tissue by detecting a positional offset between two enface image data items via image processing. The CPU 11 tracks the unit areas 5 by controlling the scan position of measurement light scanned by the optical scanner 108 such that the change of the detected position is cancelled out. The CPU 11 executes a tracking process of S11 both while the inside of each unit area 5 is scanned with measurement light and while the unit area 5 to be scanned with measurement light is changed. Accordingly, each of the plurality of unit areas 5 is suitably scanned with measurement light.

The CPU 11 acquires OCT signals from an $n^{th}$ (initial value is "1") unit area 5 by scanning the $n^{th}$ unit area 5 with measurement light via controlling of the optical scanner 108 (S13). As described above, in the embodiment, the plurality of OCT signals are acquired for the same position in the unit area 5 by scanning the same position with measurement light a plurality of times at different timing. For further details, the CPU 11 acquires a plurality of OCT signals from the plurality of measurement points on each scanning line S by scanning measurement light along each scanning line S (refer to FIG. 3) a plurality of times at different timing.

Regardless of the size of the unit area 5, the CPU 11 of the embodiment maintains the number of measurement points on each scanning line S at a predetermined upper limit value (for example, 256 in the embodiment). Accordingly, even if there is a limit to the detection speed of the light receiving element 120 at which received light signals are detected, the CPU 11 is capable of scanning each scanning line S with measurement light at suitable scan intervals. In the embodiment, the number of measurement points on the scanning line S is always maintained at the upper limit value. Alternatively, the number of measurement points on the scanning line S may be changed. For example, in a case where the size (for example, a size in a direction along the scanning line S) of the unit area 5 is a predetermined size or larger, the CPU 11 may maintain the number of measurement points on the scanning line S at the upper limit value. If the size of the unit area 5 is smaller than the predetermined size, the CPU 11 may change the number of measurement points on the scanning line S in a range smaller than the upper limit value. If effects of an increase in measurement light scan interval are small, the CPU 11 may not determine an upper limit value for the number of measurement points on the scanning line S, but may change the number of measurement points.

Subsequently, the CPU 11 acquires motion contrast data (three-dimensional motion contrast data in the embodiment) of the $n^{th}$ unit area 5 by processing the OCT signals acquired from the $n^{th}$ unit area 5 (S14).

The CPU 11 generates at least one of an $n^{th}$ enface motion contrast image and an $n^{th}$ three-dimensional motion contrast image from the acquired motion contrast data (S15). The CPU 11 displays the generated $n^{th}$ image on the display 21 (S15). In the embodiment, the display 21 displays the generated $n^{th}$ image and a plurality of buttons including an "OK" button and a "RETRY" button. The user confirms the display image, and operates a button according to whether the $n^{th}$ motion contrast data is accepted.

If the "OK" button is not operated but the "RETRY" button is operated (S17: NO), the process returns to S13, and motion contrast data of the $n^{th}$ unit area 5 is acquired again (S13 to S15). In a case where motion contrast data is acquired again, the CPU 11 may acquire motion contrast data again in a state where the data acquired in the previous routine is stored in the non-volatile memory 14 or the like, or may discard the data acquired in the previous routine, and acquire motion contrast data again. The CPU 11 may determine whether the data acquired in the previous routine is to be stored, according to an operational instruction from the user.

If the "OK" button is operated (S17: YES), the CPU 11 determines whether motion contrast data has been acquired from all the unit areas 5 arranged in the wide area 6 (S19). That is, it is determined in S19 whether the imaging of all the unit areas 5 is complete. If the imaging of all the unit areas 5 is not complete (S19: NO), the CPU 11 adds one to a counter "n" indicating the order of the unit area 5 (S21), and acquires motion contrast data from the subsequent unit area 5 (S13 to S15). Motion contrast data is acquired from each of the plurality of unit areas 5 by repeating the aforementioned process. The CPU 11 may stop the process of acquiring data from the plurality of unit areas 5 according to a specific operational instruction from the user. The CPU 11 may skip the data acquisition process for a portion of the plurality of unit areas 5 according to a specific operational instruction.

If the imaging of all the unit areas 5 is complete (S19: YES), the CPU 11 positions plural pieces of motion contrast data which has been acquired from each of the plurality of unit areas 5 (S22). As a result, motion contrast data of a range of area wider than each unit area 5 is acquired. Examples of the data pattern of a wide range of motion contrast data include two-dimensional motion contrast image data, three-dimensional motion contrast image data, and non-imaged data.

The ophthalmic imaging device 1 of the embodiment is capable of positioning the plural pieces of motion contrast data automatically or according to an operational instruction from the user. It is possible to adopt various methods as an automatic positioning method. For example, the CPU 11 may position plural pieces of motion contrast data according to information regarding the scan position of measurement light (that is, information regarding the position of the unit area 5). The CPU 11 may process each motion contrast image, and position the motion contrast images based on the connection of tissues (for example, the connection of blood vessels) or the like. The CPU 11 may match a reference image (for example, image captured by the enface observation optical system 200) to each motion contrast image, and position the motion contrast images based on matched results.

Figure 11:
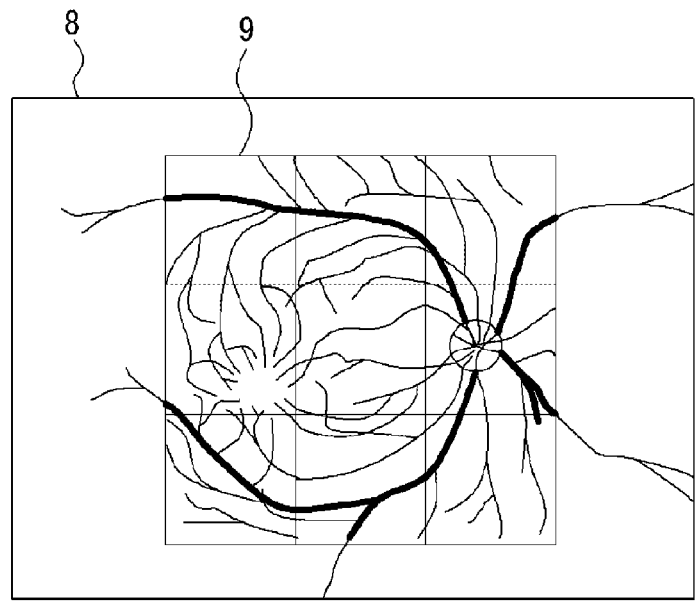
FIG. 11 is a view illustrating an example of a display mode of a motion contrast image.

An example of a method of displaying a motion contrast image on the display 21 will be described with reference to FIG. 11. In an example illustrated in FIG. 11, the CPU 11 displays a two-dimensional motion contrast image (for example, a wide two-dimensional motion contrast image 9) in a superimposed manner on a two-dimensional enface image 8 (for example, an SLO enface image, an infrared enface image, or an enface image captured by a fundus camera) captured by the enface observation optical system 200, or an OCT enface image captured by the OCT optical system 100. The CPU 11 determines a position where a two-dimensional motion contrast image is superimposed on the enface image 8, based on a position (that is, the position of the unit area 5) on the tissue where motion contrast data is acquired, and displays the two-dimensional motion contrast image on the enface image 8 in a superimposed manner. Accordingly, the user can suitably confirm, via the enface image 8, the position on the tissue where the two-dimensional motion contrast image is captured. Needless to say, a two-dimensional motion contrast image or a three-dimensional motion contrast image may be individually displayed rather than being displayed in a superimposed manner. The CPU 11 may display a two-dimensional motion contrast image, which is acquired from one unit area 5, on the enface image rather than displaying the wide two-dimensional motion contrast image 9.

The adjustment of the gradation value (contrast or brightness) of a wide motion contrast image will be described. In the embodiment, the plurality of unit areas 5 are not completely overlapped with each other. Accordingly, the CPU 11 scans each of different unit areas 5 with measurement light by controlling the driving of the optical scanner 108. As a result, the state of measurement light or the like for each unit area 5 may change, and the brightness or the like of a motion contrast image may change according to the unit area 5. For example, an image of the unit area 5 positioned in the vicinity of an end portion of a wide motion contrast image may become darker than an image of the unit area 5 positioned at the center of the wide motion contrast image. Accordingly, the CPU 11 of the embodiment reduces a difference between the unit areas 5 by adjusting the gradation value of each unit area 5. It is possible to adopt various methods as the method of adjusting the gradation value of each unit area 5. For example, as described above, a difference between the unit areas 5 may be reduced based on the gradation of superimposed portions of the plurality of unit areas 5. The CPU 11 may adjust a gradation value in the vicinity of the boundary of adjacent unit areas 5 such that a difference in brightness between one side and the other side of the boundary.

As described above, the ophthalmic imaging device 1 of the embodiment receives the designation of the wide area 6 wider than the unit area 5. The ophthalmic imaging device 1 acquires the plurality of OCT signals from each of the plurality of unit areas 5 positioned in the designated wide area 6. Motion contrast data (unit data) for each unit area 5 is acquired by processing the acquired OCT signals. A wide range of motion contrast data of a range of area wider than each unit area 5 is suitably acquired by positioning plural pieces of unit data. Accordingly, a user can easily acquire motion contrast data of a range of area wider than the unit area 5 by designating the wide area 6, the motion contrast data of which is desired to be acquired.

The ophthalmic imaging device 1 of the embodiment tracks the position of the unit area 5 on a tissue to be scanned with measurement light using enface image data of a range of area wider than each unit area 5. Accordingly, the ophthalmic imaging device 1 is capable of suitably tracking the position of each of the plurality of unit areas 5 which are not completely overlapped with each other compared to a case in which enface image data of an imaged area having a size smaller than or equal to the unit area is a tracking reference.

Every time the acquisition of motion contrast data from a unit number (one in the embodiment) of the unit area 5 is complete, the ophthalmic imaging device 1 of the embodiment receives an input of an instruction indicating that the acquired motion contrast data is accepted. Upon receiving an instruction indicating the acceptance, the ophthalmic imaging device 1 starts to acquire motion contrast data from other unit areas 5. Accordingly, a user can acquire the motion contrast data of the plurality of unit areas 5 via the ophthalmic imaging device 1 while suitably confirming that the motion contrast data acquired from each unit area 5 is suitable.

The ophthalmic imaging device 1 of the embodiment acquires the plurality of OCT signals from each of the plurality of unit areas 5 by changing the scan position of measurement light in a state where the presentation position of a fixation target with respect to the test eye E is fixed. In this case, effects of the distortion of measurement light are decreased in comparison with that in a case where OCT signals of the plurality of unit areas 5 are acquired by changing the presentation position of the fixation target. Accordingly, when the motion contrast data acquired from each of the plurality of unit areas 5 is positioned, data having the decreased effect of distortion is positioned. As a result, it is easy to suitably perform positioning.

The ophthalmic imaging device 1 of the embodiment receives the designation of the size of each unit area 5, and acquires motion contrast data from the unit area 5 of the designated size. Accordingly, a user can acquire a wide range of motion contrast data via the ophthalmic imaging device 1 via a more desirable method (for example, a method in which a short imaging time is required, or a method in which a high resolution is obtained).

In order to acquire good motion contrast data, the same position is desirably scanned with measurement light at suitable time intervals (for example, every 2.5 ms to 5 ms) a plurality of times. If there is no limit to the speed (that is, the number of times where received light signals can be detected per unit time) of the light receiving element 120 at which the light receiving element 120 is capable of detecting received light signals, even if the number of measurement points on one scanning line S is large, the scanning of measurement light can be repeated at suitable time intervals, and thus, good motion contrast data is obtained. However, there is a limit to the detection speed of the light receiving element 120. Accordingly, if the number of measurement points on the scanning line S is excessively large, a measurement light scan interval for the same position becomes longer than the suitable interval, and the quality of motion contrast data may deteriorate. In a case where the size of the unit area 5 is at least a predetermined size or larger, regardless of the designated size, the ophthalmic imaging device 1 of the embodiment maintains the number of measurement points on the scanning line S at the upper limit value. Accordingly, the ophthalmic imaging device 1 easily maintains the measurement light scan interval for the same position at the suitable interval. Even if the size of the unit area 5 (in the embodiment, the size of the unit area 5 in the direction along the scanning line S) is large, good motion contrast data is easily acquired.

In the ophthalmic imaging device 1 of the embodiment, a user designates one of the sizes of predetermined multiple types of unit areas 5. Accordingly, the user can easily select a suitable size from the sizes of the multiple types of unit areas 5 according to a priority item (for example, a reduction in measurement time or data accuracy (for example, the resolution of an image)).

In the embodiment, a user can designate a desired size from the sizes of predetermined multiple types of wide areas 6. The types of the size of the unit area 5 which can be designated by a user is determined in advance according to the types of the size of the wide area 6. Accordingly, in the ophthalmic imaging device 1, a user can easily designate the size of the unit area 5 suitable for the size of each wide area 6.

In the embodiment, if the wide area 6 is designated by a user, a plurality of unit areas 5 are automatically arranged in the designated wide area 6 at positions where the plurality of unit areas 5 are not completely overlapped with each other. Accordingly, motion contrast data is more easily acquired from a wide range of a tissue.

In the ophthalmic imaging device 1 of the embodiment, a user can designate the positions of plurality of unit areas 5 arranged in the wide area 6. Accordingly, the user can more easily acquire motion contrast data for a desired position via the ophthalmic imaging device 1.

The ophthalmic imaging device 1 of the embodiment is capable of acquiring motion contrast data of a range of area wider than the unit area 5 by positioning plural pieces of motion contrast data acquired from each of the plurality of unit areas 5. Accordingly, even if a user does not perform the operation of positioning the plural pieces of motion contrast data, a wide range of motion contrast data is suitably acquired. The ophthalmic imaging device 1 of the embodiment is also capable of positioning the plural pieces of motion contrast data according to an operational instruction input by a user.

The ophthalmic imaging device 1 of the embodiment displays an enface image on the display 21, and displays the wide area 6, which is designated by a user, on the displayed enface image. If the ophthalmic imaging device 1 receives an instruction to move the position of the wide area 6 on the enface image, the ophthalmic imaging device 1 moves the position of the wide area 6 displayed on the enface image according to the instruction. In this case, the ophthalmic imaging device 1 acquires OCT signals and motion contrast data from a tissue, which is positioned in the wide area 6 moved according to the instruction, among tissues displayed on the enface image. Accordingly, a user can suitably set a range for which a wide range of motion contrast data is acquired while observing the enface image of the tissues.

In a case where the ophthalmic imaging device 1 of the embodiment moves the wide area 6 displayed on an enface image, the ophthalmic imaging device 1 also moves the positions of the plurality of unit areas 5, which are displayed on the enface image together with the wide area 6, on the enface image together with the wide area 6. Accordingly, a user can set the range, for which a wide range of motion contrast data is acquired, at a suitable position while maintaining the disposition of the unit areas 5 in the wide area 6.

The technology disclosed in the embodiment is merely an example. Accordingly, the technology exemplified in the embodiment can be also changed.

Figure 12:
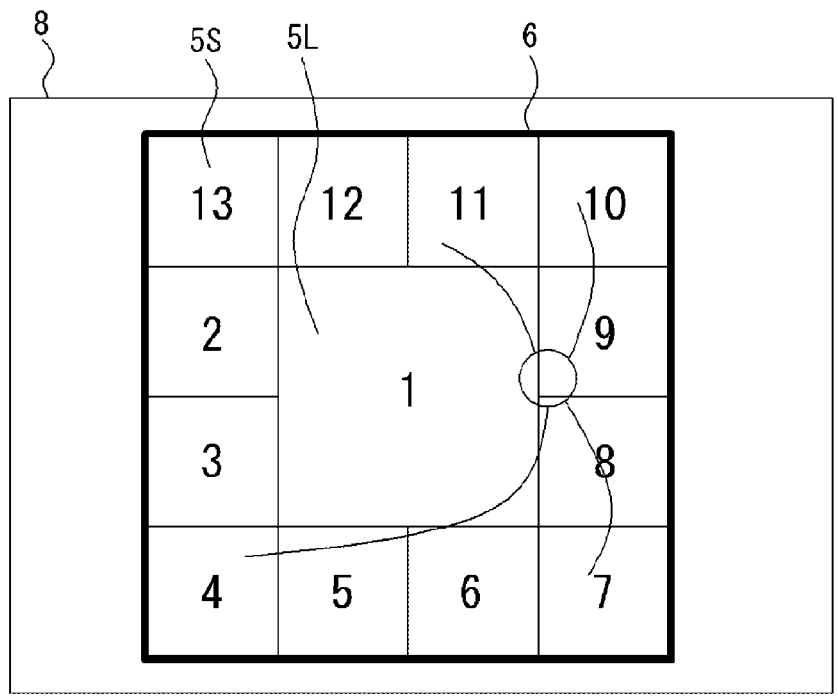
FIG. 12 is a view illustrating an example in which multiple types of unit areas 5L and 5S having different sizes are used.

A description given with reference to FIG. 12 relates to a case in which multiple types of unit areas 5, of which at least ones of the sizes and the shapes are different from each other, are used. In the embodiment, the plurality of unit areas 5 arranged in the wide area 6 have the same size and shape. Alternatively, it is also possible to use multiple types of unit areas 5, of which at least ones of the sizes and the shapes are different from each other.

In an example illustrated in FIG. 12, a unit area 5L is arranged at the center of the wide area 6. Unit areas 5S are arranged in such a way as to surround the periphery of the unit area 5L, and the longitudinal and lateral sizes of each of the unit areas 5S are one half of those of the unit area 5L. In the example illustrated in FIG. 12, the CPU 11 may set the number of measurement points on the scanning line S in the unit area 5L to be same as the number of measurement points on the scanning line S in the unit area 5S. In this case, the resolution of a motion contrast image acquired from the smaller unit area 5S is higher than that of a motion contrast image acquired from a larger unit area 5L. Accordingly, it is possible to acquire a high-resolution image of a peripheral portion, the image quality of which is likely to deteriorate due to effects of the distortion of an image. As a result, the overall quality of a wide range of motion contrast data is improved. The CPU 11 may change the number of measurement points on the scanning line S according to the type of the unit area 5. Multiple types of unit areas 5 having different shapes may be used. As described above, the ophthalmic imaging device 1 is also capable of acquiring a wide range of better motion contrast data using the multiple types of unit areas 5.

In the embodiment, the wide area 6 and the unit area 5 are designated by a user. Alternatively, the size and the shape of the unit area 5 may be fixed. In this case, if the wide area 6 is designated, the CPU 11 may arrange the plurality of unit areas of a predetermined size and shape in the wide area 6 according to the designated wide area 6.

In the embodiment, the unit area 5 has a square shape. A user designates the size of the unit area 5 of a square shape. However, the shape of the unit area 5 is not limited to a square shape. For example, the CPU 11 may receive the designation of the shape (for example, a rectangular shape, a square shape, or a circular shape) of the unit area 5, and acquire motion contrast data from the unit area 5 of the designated shape.

In the embodiment, every time the acquisition of motion contrast data from one unit area 5 is complete, an input indicating the acceptance of the data is received. Upon the receipt of the instruction indicating the acceptance, the acquisition of motion contrast data from other unit areas 5 is started. Alternatively, the CPU 11 may continuously acquire motion contrast data from each of all the unit areas 5 rather than waiting for an acceptance instruction from a user. Every time the acquisition of motion contrast data not from one unit area 5 but from the plurality (for example, two) of unit areas 5 is complete, the CPU 11 may allow a user to confirm whether the data is accepted. The CPU 11 of the embodiment allows a user to confirm data by displaying a motion contrast image, which is acquired from one unit area 5, on the display 21. Alternatively, the CPU 11 may allow a user to confirm data by displaying information (for example, a numerical value indicating the quality of an image) on the display 21, apart from an image among information regarding motion contrast data. The CPU 11 may allow a user to confirm data by notifying the user of information regarding motion contrast data via voice or the like.

In the embodiment, OCT signals are acquired from each of the plurality of unit areas by changing the scan position of measurement light in a state where the presentation position of a fixation target is fixed. As a result, effects of the distortion of measurement light are reduced. Alternatively, the CPU 11 may change the unit area 5 to be scanned with measurement light by changing the presentation position of a fixation target.

In the embodiment, after the acquisition of motion contrast data from all the unit areas 5 is complete, plural pieces of motion contrast data is positioned. Alternatively, every time motion contrast data is acquired from one or more unit areas 5, the CPU 11 may position the acquired motion contrast data.

In the embodiment, the sizes of multiple types of wide areas 6 and unit areas 5 which can be designated by a user are determined in advance. Alternatively, the sizes of the wide area 6 and the unit area 5 which can be designated may not be determined in advance. That is, the size of at least one of the wide area 6 and the unit area 5 may be suitably changed continuously or in a stepwise manner according to an instruction from a user. For example, the CPU 11 may automatically change at least one of the size and the shape of each unit area 5 and the number of unit areas 5 arranged in the wide area 6 according to a change in the size or shape of the wide area 6. The CPU 11 may automatically change at least one of the size and the shape of the wide area 6 according to a change in at least one of the size and the shape of the unit area 5, the number of unit areas 5, and the like.

In the embodiment, the plurality of unit areas 5 are arranged in the wide area 6 in a state where there are no gaps between adjacent the plurality of unit areas 5. That is, the CPU 11 arranges the plurality of unit areas 5 such that end portions of adjacent unit areas 5 adjoin each other or the unit areas 5 are partially overlapped with each other. Alternatively, the CPU 11 may arrange a plurality of unit areas 5 in a state where adjacent unit areas 5 are separated from each other.

In the embodiment, the unit areas 5 are tracked based on enface image data which is acquired before the acquisition of motion contrast data is started. However, the tracking method can be also changed. For example, the CPU 11 may acquire enface image data which is a tracking reference, while OCT signals required to acquire motion contrast data are acquired from an initial unit area 5. Also, in this case, the CPU 11 may perform tracking when the unit area 5 is changed.

What is claimed is:

1. An ophthalmic imaging device that captures an image of a test eye, the device comprising:
   an OCT optical system configured to acquire an OCT signal by scanning a tissue of the test eye with measurement light;
   a processor; and
   a memory storing computer readable instructions, when executed by the processor, causing the ophthalmic imaging device to execute:
   a wide area receiving instruction of receiving a designation of a wide area which is wider than a unit area which is an acquisition unit for acquiring motion contrast data indicating a motion of the tissue;
   a unit OCT signal acquisition instruction of acquiring a plurality of OCT signals for the same position at different timing in each of a plurality of unit areas, the plurality of unit areas being positioned in the designated wide area and being not completely overlapped with each other; and
   a unit data acquisition instruction of acquiring the motion contrast data of each of the plurality of unit areas by processing the plurality of OCT signals acquired for the same position.

2. The ophthalmic imaging device according to claim 1 further comprising:
   an enface observation optical system configured to acquire enface image data of the test eye, and repeatedly acquire the enface image data of a range of area wider than each of the plurality of unit areas,
   wherein the computer readable instructions when executed by the processor causes the ophthalmic image device to further execute:
   a tracking instruction of tracking the position of each of the plurality of unit areas, the plurality of OCT signals of which are acquired, using the repeatedly acquired enface image data according to a change in a relative position between the OCT optical system and the tissue.

3. The ophthalmic imaging device according to claim 1, wherein the computer readable instructions when executed by the processor causes the ophthalmic image device to further execute:
   an acceptance instruction receiving instruction of displaying information regarding the acquired motion contrast data on a display, and receiving an instruction indicating acceptance of the motion contrast data every time the plurality of OCT signals and the motion contrast data from the unit area is acquired a unit number of times,
   wherein upon the ophthalmic image device receives the instruction indicating the acceptance of the motion contrast data, the ophthalmic image device according to the unit OCT signal acquisition instruction and the unit data acquisition instruction starts to acquire the plurality of OCT signals and motion contrast data from other unit areas.

4. The ophthalmic imaging device according to claim 1 further comprising:
a fixation target presentation optical system that guides a line-of-sight direction of the test eye by presenting a fixation target to the test eye,
wherein the ophthalmic image device according to the unit OCT signal acquisition instruction acquires the plurality of OCT signals from each of the plurality of unit areas by changing the scanned position of measurement light scanned by the OCT optical system in a state where a presentation position of the fixation target with respect to the test eye is fixed.

5. The ophthalmic imaging device according to claim 1, wherein the computer readable instructions when executed by the processor causes the ophthalmic image device to further execute a unit area size receiving instruction of receiving a designation of a size of each unit area,
wherein the ophthalmic image device according to the unit OCT signal acquisition instruction acquires the plurality of OCT signals from the unit area of the designated size.

6. The ophthalmic imaging device according to claim 5, wherein the ophthalmic image device according to the unit OCT signal acquisition instruction scans the measurement light along each scanning line a plurality of times at different timing and acquires the plurality of OCT signals for each of a plurality of measurement positions on each of the scanning lines, and
wherein in a case where the designated size of the unit area is at least a predetermined size or larger, regardless of the designated size, the ophthalmic image device according to the unit OCT signal acquisition instruction maintains the number of measurement points on each scanning line at a predetermined upper limit value.

7. The ophthalmic imaging device according to claim 5, wherein the ophthalmic image device according to the unit area size receiving instruction receives the designation of one of the sizes of predetermined multiple types of unit areas.

8. The ophthalmic imaging device according to claim 7, wherein the ophthalmic image device according to the wide area receiving instruction receives the designation of one of the sizes of the predetermined multiple types of unit areas, and
wherein the types of the size of the unit area which can be designated by the unit area size receiving instruction are determined in advance according to each type of the size of the wide area.

9. The ophthalmic imaging device according to claim 1, wherein the computer readable instructions when executed by the processor causes the ophthalmic image device to further execute:
an arranging instruction of arranging the plurality of unit areas in the wide area, which is designated by the wide area receiving instruction, at positions where the plurality of unit areas are not completely overlapped with each other.

10. The ophthalmic imaging device according to claim 1, wherein the computer readable instructions when executed by the processor causes the ophthalmic image device to further execute:
a position receiving instruction of receiving an instruction to designate the positions of the plurality of unit areas which are arranged in the wide area designated by the wide area receiving instruction,
wherein the ophthalmic image device according to the unit OCT signal acquisition instruction acquires plurality of OCT signals from the unit area at the designated position.

11. The ophthalmic imaging device according to claim 1, wherein the computer readable instructions when executed by the processor causes the ophthalmic image device to further execute:
a wide-range data acquisition instruction of acquiring the motion contrast data of a range of area wider than each of the plurality of unit areas by positioning the plural pieces of motion contrast data acquired from each of the plurality of unit areas.

12. The ophthalmic imaging device according to claim 1, wherein the ophthalmic image device according to the unit OCT signal acquisition instruction acquires the plurality of OCT signals from each of the multiple types of unit areas which are positioned in the wide area, at least ones of the sizes and the shapes of the multiple types of unit areas being different from each other.

13. The ophthalmic imaging device according to claim 1, further comprising:
an enface observation optical system configured to acquire enface image data of the test eye, and capture an enface image of a tissue of the test eye;
wherein the computer readable instructions when executed by the processor causes the ophthalmic image device to further execute:
an area display controlling instruction of displaying the captured enface image on a display, and displaying the wide area, which is designated by the wide area receiving unit, on the enface image;
a movement instruction receiving instruction of receiving an instruction to move the position of the wide area on the enface image; and
an area moving instruction of moving the position of the wide area on the enface image according to the instruction to move the position of the wide area,
wherein the unit OCT signal acquisition instruction of acquiring the plurality of OCT signals from the tissue, which is positioned in the wide area moved by the area moving instruction, among tissues displayed on the enface image.

14. The ophthalmic imaging device according to claim 13, wherein the ophthalmic image device according to the area moving instruction moves the positions of the plurality of unit areas in the wide area on the enface image together with the wide area.

15. The ophthalmic imaging device according to claim 1, wherein the computer readable instructions when executed by the processor causes the ophthalmic image device to further execute a determination instruction of determining whether the motion contrast data is accepted every time the motion contrast data of one unit area is acquired.

16. The ophthalmic imaging device according to claim 1, wherein the computer readable instructions when executed by the processor causes the ophthalmic image device to further:
a display controlling instruction of displaying the motion contrast data on a display every time the motion contrast data of one unit area is acquired; and
an acceptance instruction receiving instruction of receiving an instruction input from a user which indicates whether or not to accept the motion contrast data displayed on the display by the display controller.

17. The ophthalmic imaging device according to claim 1, wherein each unit area is a two-dimensional area in an XY direction.

18. A non-transitory computer readable recording medium storing an ophthalmic imaging program that is executed by a control device which controls an operation of an ophthalmic imaging device configured to capture an image of a test eye, wherein the ophthalmic imaging device includes an OCT optical system configured to acquire an OCT signal by scanning a tissue of the test eye with measurement light, the ophthalmic imaging program, when executed by the control device of the ophthalmic imaging device, causing the ophthalmic imaging device to execute:

receiving a designation of a wide area which is wider than a unit area which is an acquisition unit for acquiring motion contrast data indicating a motion of the tissue;

acquiring a plurality of OCT signals for the same position at different timing in each of a plurality of unit areas, the plurality of unit areas being positioned in the designated wide area and being not completely overlapped with each other; and acquiring the motion contrast data of each of the plurality of unit areas by processing the plurality of OCT signals acquired for the same position, wherein motion contrast data of a range of area wider than each unit area is acquired by positioning the plural pieces motion contrast data acquired from each of the plurality of unit areas.

* * * * *